United States Patent
Martens et al.

(10) Patent No.: US 10,506,993 B2
(45) Date of Patent: Dec. 17, 2019

(54) DUAL ENERGY DIFFERENTIAL PHASE CONTRAST IMAGING

(71) Applicant: KONINKLIJKE PHILIPS N.V., Eindhoven (NL)

(72) Inventors: Gerhard Martens, Henstedt-Ulzburg (DE); Udo Van Stevendaal, Ahrensburg (DE)

(73) Assignee: KONINKLIJKE PHILIPS N.V., Eidhoven (NL)

( * ) Notice: Subject to any disclaimer, the term of this patent is extended or adjusted under 35 U.S.C. 154(b) by 0 days.

(21) Appl. No.: 15/511,362

(22) PCT Filed: Aug. 26, 2016

(86) PCT No.: PCT/EP2016/070148
§ 371 (c)(1),
(2) Date: Mar. 15, 2017

(87) PCT Pub. No.: WO2017/032864
PCT Pub. Date: Mar. 2, 2017

(65) Prior Publication Data
US 2018/0153486 A1 Jun. 7, 2018

(30) Foreign Application Priority Data
Aug. 26, 2015 (EP) .................................... 15182578

(51) Int. Cl.
*A61B 6/04* (2006.01)
*A61B 6/00* (2006.01)
(Continued)

(52) U.S. Cl.
CPC .......... *A61B 6/4042* (2013.01); *A61B 6/4241* (2013.01); *A61B 6/4291* (2013.01);
(Continued)

(58) Field of Classification Search
CPC ... A61B 6/4035; A61B 6/4042; A61B 6/4241; A61B 6/4291; A61B 6/482; A61B 6/484; A61B 6/06; A61B 6/4021; A61B 6/4233; A61B 6/502; A61B 6/032; A61B 6/4092; A61B 6/4441; A61B 6/00; A61B 6/5205; A61B 6/035; A61B 6/40; A61B 6/483; A61B 6/505; A61B 6/5235; A61B 6/583; G02B 5/1838; G21K 1/10; G21K 2207/005; G21K 1/025; G21K 1/06; G21K 1/067; G01N 2223/1016; G01N 23/04; G01N 23/20075; G01N 2223/206; G01N 23/087; H05G 2/001
USPC ............................................. 378/37, 62, 36
See application file for complete search history.

(56) References Cited

U.S. PATENT DOCUMENTS 9,063,055 B2 6/2015 Ouchi
9,649,082 B2 5/2017 Wischmann
(Continued)

FOREIGN PATENT DOCUMENTS

DE 102014213817 6/2015
EP 0984302 3/2000
(Continued)

*Primary Examiner* — Irakli Kiknadze
(74) *Attorney, Agent, or Firm* — Larry Liberchuk

(57) ABSTRACT

A grating based interferometric X-ray imaging apparatus having an interferometer (IF). The interferometer comprises at least one grating (G1). The grating (G1) is tiltable relative to an optical axis of the X-ray imaging apparatus. This allows changing a design energy of the X-ray imaging apparatus.

12 Claims, 9 Drawing Sheets

(51) Int. Cl.
*G02B 5/18* (2006.01)
*G21K 1/10* (2006.01)

(52) U.S. Cl.
CPC .............. *A61B 6/482* (2013.01); *A61B 6/484* (2013.01); *G02B 5/1838* (2013.01); *G21K 1/10* (2013.01); *G21K 2207/005* (2013.01)

(56) References Cited

U.S. PATENT DOCUMENTS

| | | |
|---|---|---|
| 2011/0235780 A1 | 9/2011 | Tada |
| 2011/0243300 A1 | 10/2011 | Kaneko |
| 2013/0223595 A1 | 8/2013 | Vogtmeier |
| 2013/0308751 A1* | 11/2013 | Koehler ............... G21K 1/06 378/36 |
| 2014/0226783 A1 | 8/2014 | Ning |
| 2014/0270060 A1 | 9/2014 | Date |
| 2014/0328457 A1 | 11/2014 | Stutman |

FOREIGN PATENT DOCUMENTS

| | | |
|---|---|---|
| RU | 53573 | 5/2006 |
| WO | 2010/109390 | 9/2010 |
| WO | 2010/146498 | 12/2010 |
| WO | 2012/063169 | 5/2012 |
| WO | 2015/038794 | 3/2015 |
| WO | 2015/064723 | 5/2015 |
| WO | 2016/177588 | 11/2016 |

\* cited by examiner

DUAL ENERGY DIFFERENTIAL PHASE CONTRAST IMAGING

CROSS REFERENCE TO RELATED APPLICATIONS

This application is the U.S. National Phase application under 35 U.S.C. § 371 of International Application No. PCT/EP2016/070148, filed Aug. 26, 2016, published as WO 2017/032864 on Mar. 2, 2017 on, which claims the benefit of European Patent Application Number 15182578.3 filed Aug. 26, 2015. These applications are hereby incorporated by reference herein.

FIELD OF THE INVENTION

The invention relates to an X-ray imaging apparatus, a method of operating an X-ray imaging apparatus, a computer program element, and a computer readable medium.

BACKGROUND OF THE INVENTION

Grating-based interferometric differential-phase contrast and dark-field imaging is a promising technology that adds diagnostic value in particular in the area of chest imaging since the dark-field signal channel is highly sensitive to changes of the micro-structure of lung tissue.

However, adapting grating based interferometric imaging equipment to different imaging tasks is remarkably cumbersome at times. For instance, the adaptation may involve difficult and time consuming adjustments of an interferometer used in the imaging.

SUMMARY OF THE INVENTION

There may be a need for alternative X-ray imaging apparatuses.

The object of the present invention is solved by the subject matter of the independent claims where further embodiments are incorporated in the dependent claims. It should be noted that the following described aspect of the invention equally apply to the method of operating an X-ray imaging apparatus, to the computer program element, and to the computer readable medium.

According to a first aspect of the invention there is provided an X-ray imaging apparatus comprising:

an X-ray source configured to emit X-radiation;
an X-ray detector configured to detect said X-radiation;
an interferometer arranged between said X-ray source and said detector, said interferometer comprising at least one (first) interferometric grating structure;
wherein said at least one interferometric grating structure is tiltable around an axis perpendicular to an optical axis of said imaging apparatus, the at least one grating thereby capable of being oriented at different tilt angles relative to said axis.

Tilting of the interferometric grating structure allows adjusting the imaging apparatus, in particular its interferometer, to different design energies as the tilting leads to an inclined illumination of the gratings structure and thus to a change of an effective Talbot distance through the interferometer.

According to one embodiment, the imaging apparatus includes at least one further grating, referred to herein as a source grating, arranged between said interferometric grating and said X-ray source, said source grating structure configured to convert said emitted X-radiation into X-radiation with increased coherence, and said source grating structure likewise tiltably arranged around a second axis parallel to the first axis, so as to maintain or to re-establish a spatial relationship (in particular parallelism) between said source grating and the at least one interferometric grating. In particular the two gratings are to remain substantially parallel or their parallelism should be restored after the rotation if the gratings are independently rotatable. When tilted, the normal of the plane of the interferometer grating(s) and/or source grating is not parallel to the optical axis. Yet more specifically, the gratings are rotatable about respective axes that run parallel to the course of the direction of the gratings rulings (trenches and ridges).

According to one embodiment, the said tilt angle is any one of approximately +/−30°, +/−45° and +/−60°. "+" and "−" indicate orientation (clockwise/counterclockwise) of the tilting or rotation and 0° indicates the configuration of perpendicular illumination, in other words, a configuration where the normal of the plane of the gratings is parallel to the optical axis. As mentioned above, the tilting of the source grating and/or of the at least one interferometric grating changes the design energy of said interferometer. In other words, the different tilt angels allow adjusting the imaging system to range of different design energies. In particular, in the configuration where the gratings are not tilted (normal irradiation), the system is configured to a certain ground design energy E0 and the tilting angle allows scaling up this ground design energy by a scale factor. For instance, +/−60° allows for a two-fold scale up.

According to one embodiment, the imaging system comprises a grating adapter mechanism to adapt for an effective grating pitch in relation to the source grating (G0) and/or in relation to the at least one interferometer. In either words, the adapter may operate on or relation to the source grating or in relation to the one or two gratings (G1,G2) of the interferometer. The mechanism allows building a new or effective pitch. This may be achieved by exchanging one of the gratings for another or by combining gratings together to build an effective pitch from existing pitches. The new or effective pitch is configured to fit to the tilted grating geometry and is to ensure that certain grating design rules for Talbot or Lau-Talbot interferometers are observed. In particular, these rules impose certain functional relationships between the gratings pitches and the length of distances or "paths" between source grating and interferometer and the path length across the interferometer.

More specifically, and according to a preferred embodiment, the grating adapter mechanism is a source grating adapter mechanism. It is configured to i) exchange the source grating structure for a new source grating structure having a pitch different from a pitch of the source grating or ii) to at least combine said source grating structure with another source grating structure having a pitch different from a pitch of the source grating, so as to compensate for a change in effective path length through a space between said source grating and said interferometer, said change in effective path length being caused by either one of said tilt angles. In other words, the grating adapter mechanism operates only on the source grating and not on the interferometric gratings G1,G2. This allows a simple implementation.

According to one embodiment, the combiner operation performed by the source grating adapter mechanism is achieved by superimposing the two source gratings or by sliding the two source gratings relative to each other when the two source gratings are at least partly superimposed onto each other, so as to form a double decker grating structure having an effective pitch that compensates for said change in effective path length caused by either one of said tilt angles.

According to one embodiment, the X-ray imaging system comprises a translator stage configured to translate, relative to the optical axis, the at least one interferometric grating and/or the source grating According to one embodiment, the interferometer further comprises a further grating structure (G2), wherein the further grating structure (G2) is likewise tiltably arranged around a third axis parallel to said first axis, so as to maintain or to re-establish a spatial relationship between said at least one interferometric grating (G1) and/or the source grating (G0).

According to one embodiment, the interferometric grating and said further grating structure are arranged on mutually opposite sides of an examination region of the X-ray imaging apparatus.

Alternatively, and according to one embodiment, the further interferometric grating structure and the interferometric grating are arranged on the same side of an examination region of the X-ray imaging apparatus.

The term "further grating structure" is either a separate, discrete or standalone interferometric grating in addition to the first interferometric grating. The further interferometric structure may be part of the interferometer, so the interferometer comprises two gratings. But the further interferometric structure may also be part of other imaging equipment of the system such as the detector. In some embodiments, it is the detector itself that forms the further interferometric structure.

The proposed system allows for a convenient way to adapt the system for different design energies. In particular this can be achieved without changing the distance between the source grating and the interferometer. Also, there is no need to change aspect ratios of the interferometric gratings as rotation around an axis parallel to direction of the grating rulings has been found to automatically yield a corresponding scale up of grating heights thanks to the inclined illumination.

According to one embodiment, the system further comprises an X-radiation filter configured to broaden a spectral window around a design energy for a given tilt angle to facilitate collection of spectral information. The spectral (energy) window defines the range of design energies for any given grating (s) inclination. The configuration and arrangement of the filter allows achieving this spectral window broadening by harnessing the fact that, for non-parallel beam geometries, there is a design-energy versus fan-angle dependency. In other words, design energies different from the one that corresponds to the chosen inclination can be achieved because the respective changes of the effective Talbot distances through the interferometer vary with fan angle.

More specifically, and according to one embodiment, the X-radiation filter has a plurality of filter elements configured for different K-edge energies. The filter elements are arranged across the optical axis in an ascending or descending order in sequence according to their respective K-edge energies. The respective thickness and or material of the respective filter elements are configured to that the respective transmission functions of the different filter elements are configurable in a "balanced" fashion so as to achieve better separation of the spectral information.

The X-ray imaging apparatus according to the present invention allows for useful application in a clinical environment such as a hospital. More specifically, the present invention is very suitable for application in imaging modalities such as mammography, diagnostic radiology and interventional radiology for the medical examination of patients. In addition, the present invention allows for useful application in an industrial environment. More specifically, the present invention is very suitable for application in non-destructive testing (e.g. analysis as to composition, structure and/or qualities of biological as well non-biological samples) as well as security scanning (e.g. scanning of luggage on airports).

According to another aspect, there is provided a method for operating an X-ray imaging apparatus having an interferometer arranged between an X-ray source and a detector, said interferometer comprising at least one interferometric grating structure:

receiving a specification of a design energy for the X-ray imaging apparatus; and in response to the specified design energy, tilting said grating relative to an optical axis of the X-ray imaging apparatus.

BRIEF DESCRIPTION OF THE DRAWINGS

Exemplary embodiments of the invention will now be described with reference to the following drawings wherein.

DETAILED DESCRIPTION OF EMBODIMENTS

Figure 1:
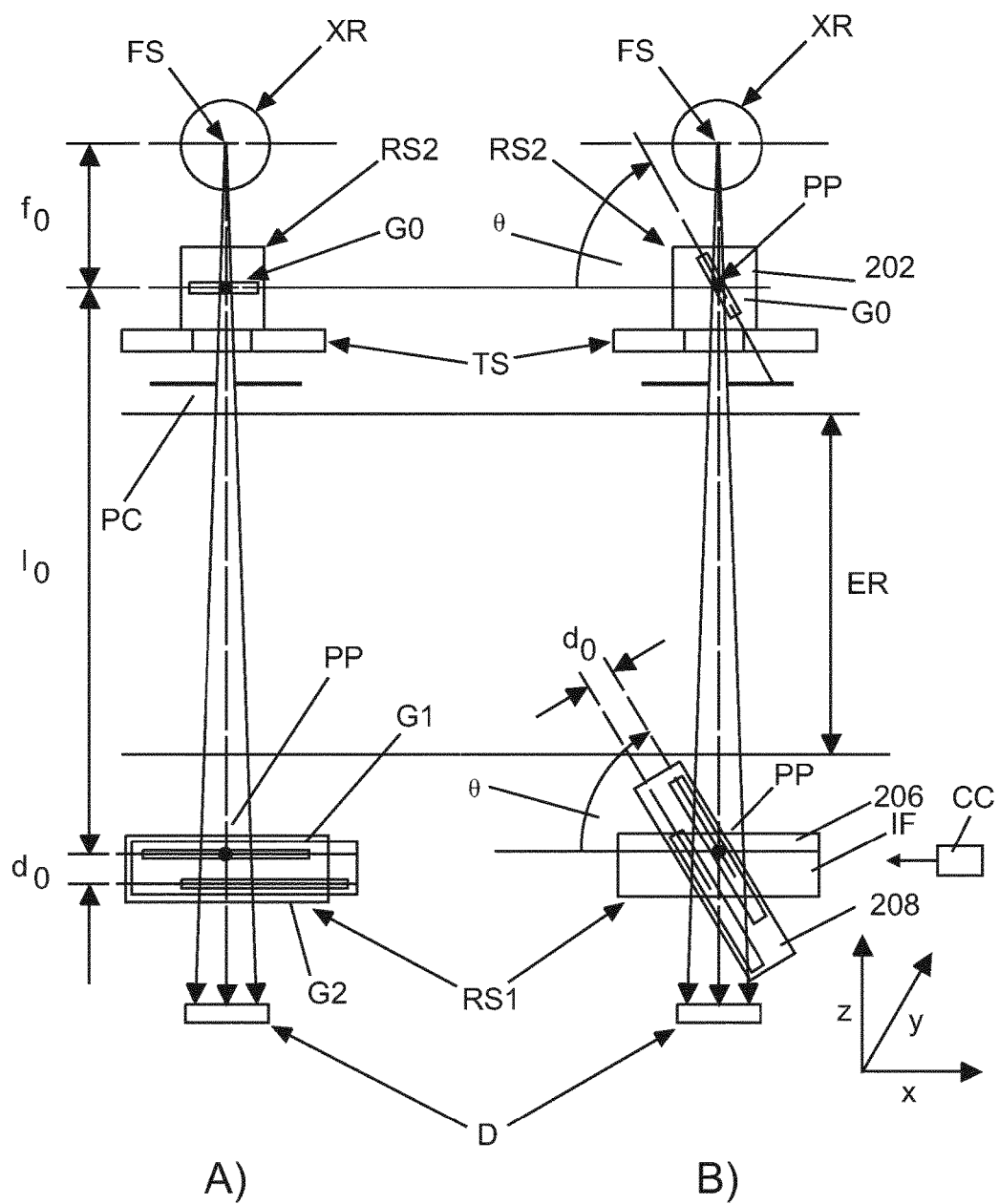
FIG. 1 shows views of different states of an X-ray imaging apparatus.

FIG. 1 affords two different side elevation views of an X-ray imaging apparatus at two different states shown in pane A and pane B respectively. The X-ray imaging apparatus comprises an X-ray source XR, a radiation sensitive detector D arranged across an examination region ER opposite said source XR. The examination region ER is configured to receive at least a part of an object OB to be imaged. Preferably, the X-ray source is operable at different voltages to produce X-radiation at different energies. The X-ray imaging apparatus further comprises an interferometer IF arranged between the X-ray source and the detector. In the following it will be convenient to introduce a reference frame of axis X, Y, and Z to better explain operation of the X-ray imaging apparatus as proposed herein. Axis X, Y define the image plane or plane of the field of view of the detector D. For instance, axis X, Y may be taken to extend, respectively, along two adjoining edges of the detector D. Perpendicular to the image plane X, Y is axis Z. This axis corresponds in general to the propagation direction of the X-ray beam which emanates a focal spot FS of the X-ray source XR. Also, axis Z is parallel to the optical axis of the X-ray imaging apparatus. The optical axis runs form the focal spot FS of the source XR to the center of the image plane of the detector D. In one embodiment there is also a pre-collimator PC as shown in the FIG. 1 arranged between the object OB and the X-ray source XR. According to one embodiment, instead of or in addition to the pre-collimator PC, there is a post-collimator (not shown) between the object OB and the detector D.

Referring now in more detail to FIG. 1 in particular to pane A of FIG. 1, the imager IM has a multi-channel imaging capability that is at least partly afforded by the interferometer IF built into the X-ray imaging apparatus. "Multi-channel imaging", as used herein, means in particular the capability of imaging for i) a spatial distribution of refraction (phase contrast imaging) activity caused by the object OB and/or ii) spatial distribution of small angle scattering (dark field imaging) activity as caused by the imaged object. In addition thereto, the more traditional way of imaging for spatial distribution of absorption in the object OB may also be possible. This type of multi-imaging capability is sometimes referred to as DPCI (differential phase contrast imaging), but, this does not exclude imaging for the other image signals, dark-field and/or absorption.

In one embodiment, the interferometer IF comprises two grating structures G1 and G2 although single grating interferometers (having only a single grating G1) are not excluded herein and will be described later below. The grating G1 is either an absorption grating or phase shift grating whereas G2 is an absorption gating. The gratings are manufactured by photo lithographically processing suitable substrates such as a silicon wafer (rectangular or even square shaped but other shapes may also be called for in other contexts). A pattern of periodic rulings is formed in those substrates as a sequence of parallel trenches, with any two neighboring trenches separated by bars or ridges. In FIG. 1, the rulings (that is, trenches and ridges) run along the Y-direction, that is, extend into the drawing plane in FIG. 1. The trenches may be filled with suitable filling material such as gold or other to cause a desired phase shifting behavior. The ruling patterns are preferably one dimensional but may also be two dimensional such as to confer a checker board pattern in which there are two sets of trenches: one set runs in the Y-direction, the other runs across the first in the X-direction. In the 1D example the rulings extend only in one direction across the surface of the substrate.

Preferably the X-ray detector D is a 2D full view X-ray detector either planar or curved. A plurality of detector pixels are arranged in rows and columns as an array to form a pixelated 2D X-ray radiation sensitive surface capable of registering X-ray radiation emitted by the X-ray source. Alternatively the X-ray detector D may also be arranged as a plurality of discreetly spaced individual lines of detector elements. Such X-ray detector is sometimes referred to as a "line detector" arrangement. The detector D is either of the energy integrating type or is, alternatively, of the energy resolving type (such as a photon counting detector).

The X-ray detector D and the X-ray source are spaced apart to form an examination region ER. The examination region is suitably spaced to receive the object OB to be imaged. The object OB may be inanimate or animate. For instance the object may be a piece of luggage or other sample to be imaged such as in non-distractive material testing etc. Preferably, however, a medical context is envisaged where the (animate) "object" is a human or animal patient or is at least an anatomic part thereof as it not always the case that the whole of the object is to be imaged but only a certain anatomic region of interest.

In one embodiment, the interferometric grating structures G1 and G2 are arranged in between the X-ray source XR and the X-ray detector D so that the examination region ER is defined between the X-ray source and the interferometer IF. More specifically, the X-ray source XR has a focal spot FS from which the X-ray radiation beam emerges. It is the space between the focal spot FS and the X-ray detector's radiation sensitive surface where the two grating structures G1 and G2 are arranged with the examination region then being formed by the space between the focal spot and the grating D1. It will be convenient in the following to refer to the grating G1 as the phase grating and to grating G2 as the analyzer grating. Functionally, the grating G1 is either an absorber grating or preferably a phase shift grating, whereas G2 is an absorber grating. However other functional combinations are not excluded herein.

In some embodiments, there is, in addition to the interferometric gratings G1, G2 of the interferometer IF, a further grating G0 which will be referred to herein as the source grating. The source grating G0 is arranged in proximity at distance f0 from the focal spot FS of the X-ray source. For instance, the source grating G0 may be arranged at the egress window of a housing of the X-ray tube unit XR. If there is a source grating, the examination region is between the source grating G0 and the interferometer IF, in particular between G0 and G1. The function of the source grating G0 is to make the emitted radiation at least partly coherent. In other words, the source grating G0 can be dispensed with if an X-ray source is used which is capable of producing native coherent radiation.

During an imaging operation, the at least partly coherent radiation emerges downstream the source grating G0 (if any), passes then through the examination region ER and interacts with the object OB therein. The object then modulates attenuation, refraction, and small angle scattering information onto the radiation which can then be extracted by operation of the interferometer IF gratings G1 and G2. More particularly the gratings G1, G2 induce an interference pattern which can be detected at the X-ray detector D as fringes of a Moiré pattern. Yet more particularly, if there was no object in the examination region there is still an interference pattern detectable at the X-ray detector D, called the reference pattern which is normally captured during a calibration imaging procedure. The Moiré pattern comes about by especially adjusting or "de-tuning" the mutual spatial relationship between the two gratings G1 and G2 by inducing a slight flexure for instance so that the two gratings are not perfectly parallel. Now, if the object is resident in the examination region and interacts with the radiation as mentioned, the Moiré pattern, which is now more appropriately called the object pattern, can be understood as a disturbed version of the reference pattern. This deviation from the reference pattern can then be used to compute a desired one, or two or all of the three images (attenuation, phase contrast, dark field). For good imaging results, the detuning of the gratings G1, G2 is such that a period of the Moiré pattern should extend for a few of its cycles (two or three) across the field of view of the detector. The Moiré pattern can be Fourier-processed for instance to extract the at least one (in particular all) of the three images. Other types of signal processing such as phase-stepping techniques are also envisaged herein.

The interferometer IF as described above is what is commonly referred to as a Talbot-Lau interferometer. Much of the accuracy of the imaging capability of the interferometric X-ray apparatus rests with the distinctness with which the Moiré pattern or interference pattern is detected at the detector D. Said distinctness can be quantified by the interferometric concept of "visibility". Visibility is an experimentally verifiable quantity defined for instance as the ratio $(I_{max}-I_{min})/(I_{max}+I_{min})$. Said differently, the visibility can be understood as the "modulation depth" of the interference pattern, that is, the ratio of fringe amplitude and the average of fringe oscillation. The visibility of the interference pattern is in turn a function of "design energy" at which the x-radiation (as produced by the X-ray source) illuminates the interferometer and the source grating G0 (if any). The design energy is the energy at which the interference pattern has the maximum visibility. Each interferometric set up is in general adjusted to a certain design energy or at least to certain design energy bandwidth around a design energy value. Examples for suitable design energies are for instance 25 keV or 50 keV but these numbers are purely exemplary. Operating the X-tube at energies different from the design energy or at least at energies outside the bandwidth will result in Moiré patterns of lower visibility and hence an overall degradation of image quality. It is also inefficient in terms of energy consumption and dose incurred to operate for instance at an energy higher than the design energy.

The chosen design energy for the X-ray imaging apparatus is usually a function of the nature of the object one wishes to image. Higher design energies are called for thicker or denser objects. Chest X-rays for instance usually require higher design energy than do thinner anatomical parts such as arms or legs because of the longer in-tissue path lengths involved. This is because, for achieving good imagery, it must be ensured that a sufficient fraction of the X-ray beam actually passes through the object to be detectable at all at the detector.

Furthermore, the choice of a certain design energy imposes restrictions on the interferometric and source grating set up. The interferometric set up includes one or more (in particular all) of the following design parameters: there is the intra-grating distance d0, or Talbot distance, which is the distance of a path along the optical axis of the imaging system between grating G1 and grating G2. There is also the distance l0 between the source grating G0 (if any) and the interferometer IF, that is, the distance along the optical axis from the G0 and analyzer grating G1. This distance l0 will be referred to herein as the "source grating distance".

The interferometric or source grating set up further includes structural properties of the gratings themselves. Said structural properties include pitches p0, p1 and p2 of the three gratings, respectively and the aspect ratios of the source grating G0 and of G1 and/or G2. "Pitch" is the spatial period of the grating rulings. The aspect ratio describes the ratio between the height of the respective trenches formed in the grating's substrate and the distance between two neighboring trenches. Aspect ratios in the order of 30-50 for instance are not unheard of, which means that the respective height of the trenches is 30-50 times the distance between two neighboring trenches. For example, aspect ratios in the order of 30-40 having a trench height of 30-40 micrometers call for inter-trench distances of about 1 micrometer. Such micro structures are difficult to produce and in the past they had to be adapted to different design energy requirements. For instance, as the source grating G0 acts as an absorber grating, this imposes certain requirements on the trench height required in order to perform this function properly. Increasing the energy with which the energy source operates to achieve the desired energy will in general mean for a given fixed grating height that the absorption characteristic of the source grating decreases. This will then lead to incoherent radiation emerging downstream the source grating G0 which in turn will compromise the function of the interferometer. Similar demands are required for the analyzer grating G2 (also configured in general as an absorber grating) which operates essentially to scale up the interference pattern as produced by the G1 source in order to make the interference pattern detectable at the detector for a given resolution. Also, grating G1 is adapted to produce the interference pattern down-stream at the desired Talbot distance (where the absorber grating G2 is positioned) with a precisely defined phase shift (usually $\pi$ or $\pi/2$). Again, to ensure that the interference pattern is precisely replicated at the desired Talbot distance at the required phase shift, a suitable aspect ratio is required for the specific design energy that is desired for a given imaging task.

In one embodiment, the proposed X-ray imaging apparatus is capable of operating at different design energies whilst maintaining the dimension (in Z direction) of the X-ray imaging apparatus without necessarily changing the aspect ratios of the interferometer gratings G1 and G2. More particularly, the distance between the focal spot and the detector can remain the same for any of the chosen design energies. In particular, in one embodiment the X-ray imaging operating is operable at the double of a certain given design energy E0. This adaptability to different design energies is achieved by inclined or oblique lamination of the interferometric gratings (illustrated in view B of FIG. 1), as compared to normal incident illumination as shown in view A of FIG. 1. More specifically, it is proposed herein to arrange the interferometer IF to be tiltable relative to the optical axis of the system. That is, the normal of the plane of the interferometer grating(s) G1 can be adjusted to be no longer parallel to the optical axis. Yet more specifically, the grating G1 is rotatable about the Y-axis, that is, around an axis that runs parallel to the course of the trenches of the grating. The rotation angle can be measured clockwise $+\theta$ or anti-clockwise $-\theta$. The rotation angle $\theta$ corresponds to the tilt angle between the normal of the plane of the grating and the optical axis. In 2D gratings, one may rotate around Y axis or the X axis. Being able to operate at different design energies affords dual energy imaging capability which allows producing images for material decomposition. More specifically, dark field or phase contrast images or absorption images for different material types can be produced. Also, the absorption signal can be decomposed into contributions from Compton scattering and photoelectric absorption, etc.

An arrangement where the interferometer IF is rotated by an exemplary rotation angle $\theta=60°$, is shown in pane B of FIG. 1. If the interferometer comprises two gratings, G1, G2, as shown in FIG. 1, both are rotatable around respective rotation axes by the required angle so as to remain parallel at all times or at least to maintain the previously adjusted de-tuning to achieve the Moiré reference pattern. The two gratings G1 and G2 are rotatable simultaneously or independently. The respective rotation axes of G1 and G2 are parallel to each other and to the Y-axis. If the apparatus also comprises a source grating G0 this too is rotatable around another rotation axis parallel to the respective rotation axes of G1 and G2, so as to remain parallel to the interferometer gratings G1, G2 of interferometer IF. The respective rotations of the interferometer IF and the source grating G can be effected by respective actuator mechanisms (also referred to herein as rotation stages) RS1 and RS2, respectively.

More specifically, a rotation stage RS2 for the source grating G0 can be implemented by using a piezo-electric actuator or a stepper motor or similar. Yet more specifically, and according to one embodiment, the G0 substrate is framed in a framelet (not shown). The grating framelet is rotatably arranged via at least one, preferably two, pivot points PP in a mounting cage 202. The one or more pivot points define a rotation axis that runs through the center of the grating G0 parallel to the direction of the grating rulings. In one embodiment, a set of two pins at opposite sides of the framelet are formed. The pins are received in respective recess in the mounting cage 202 to so afford a rotatable mounting of the framelet and hence of the grating G0. In the view of FIG. 1B, the rotation axis extends perpendicularly into the drawing plane. More specifically, the rotation axis through the respective gratings is perpendicular to the normal of the plane defined by the respective gratings and passes through the center of gravity of the grating G0. The mounting cage 202 and the framelet should be made from material of sufficient stiffness such as aluminum, or hardened steel, etc. The, for instance piezo-electric, actuator may then be applied to the framelet to effect the rotation, relative to the optical axis, of the framelet, and hence of the grating G0 arranged therein. In the embodiment where the grating is a 2D grating, rotation is switchable either around the Y-axis parallel to one set of trenches or round the X-axis parallel to the other set of trenches. This rotatability around the two orthogonal axes can be implemented for instance by mounting two framelets in a nested fashion in two gimbals, each having a pair of pins, the pairs arranged orthogonal to each other on respective one of the two framelets. Each of the framelets in the gimbals can be locked to ensure that the grating rotates only around the X or Y axis, as desired for a given imaging task. The selection of the rotation around X- or Y can be done manually or automatically via catcher mechanism controllable by a suitable actuator mechanism, such as electro-magnetic or otherwise.

A similar construction to effect the tilting with respect to the optical axis is also envisaged for the rotation stage RS for the interferometer IF. That is, in one embodiment, the two gratings G1 and G2 are together arranged in a double frame or "box" 206 to form the interferometer, with grating G1 on top of grating G2 when viewed along the negative Z direction toward the detector D. The interferometer box 206 is then rotatably arranged around a rotation axis at one or preferable two pivot points in mounting cradle 208. Again, as with grating G0, the rotation axis of the interferometer IF extends perpendicular into the drawing plane of FIG. 1. The rotation axis passes through the center of the grating G1 or G2 or is arranged halfway between the two gratings and passes through opposite sides of the interferometer box. As similar pin-in-recess mounting can be used as described above for RS1 to afford rotatability of the gratings G1, G2. To ensure a sufficient field of view even when the interferometer is rotated, the two gratings G1,G2 are slidable relative to each other as shown in FIG. 1. In one embodiment, the gratings slide away from each other in response to a request for a certain rotation angle θ≠0° (and hence a certain design energy) to cover a larger FOV and, for θ=0°, slide back towards each other, with G1 aligned atop G2.

In a preferred embodiment, one or both of rotation stages RS1, RS2 are based on piezoelectric actuators but other options, such as stepper motors or others are also envisaged herein. In some embodiments, the source grating G0 and the interferometer IF are rotatable independently from each other. In one embodiment, even the gratings G1, G2 are independently rotatable. Alternatively, the respective actuator mechanisms RS1 and RS2 are mechanically coupled by a suitable gearing mechanism so as to achieve a simultaneous rotation of the source grating G0 and the interferometer IF. Also, in one embodiment, the gratings G1, G2 are mechanically coupled to be rotatable concurrently together so as to better maintain their mutual alignment.

If the imaging apparatus is of the scanning type, there is a relative motion induced, during the image acquisition, between the object OB to be imaged and the X-ray source XR and/or the detector D. The scanning system can be implemented according to different embodiments. The scanning motion can be linear or curved, eg a pendulum motion around a pivot point which may or may not be situated at the focal spot FS of the X-ray source XR. In one embodiment there is a scan arm which is used to scan the object OB. This is the case for instance in some mammography imaging systems. The scan arm may be used to move both, detector D and the interferometer IF, relative to the object during the scan. In some (but not necessarily all) of these embodiments, the area of the detector D is essentially coextensive with the interferometer footprint (ie, the area of the grating(s)). Alternatively, the scan arm only includes the interferometer and only this is scanned relative to a stationary detector which is preferably but not necessarily a full field 2D detector having preferably, but not necessarily, a larger area than the interferometer footprint. In either one of these scanning system embodiments, at least the interferometric gratings and the source gratings can be rotatably arranged around their respective axes perpendicular to the optical axis on or within the scan arm as described above. In other embodiments, the scanning system is a slit scanning-system where the pre-collimator PC (or the post collimator) is configured to follow the scanning motion and is arranged as a slit collimator to divide the beam into one or more relatively narrow slit beams that each illuminate a respective part of the detector. If the detector is arranged as a series of one or more line detectors, each detector line is illuminated by respective ones of the slit beams at a time.

Turning now back to the rationale for having the gratings rotatably arranged: assuming that the above mentioned design parameters have been set up for certain a "primary" design energy E0 for normal radiation at θ=0° (see FIG. 1A), geometric considerations carried out by the Applicant have shown that the respective rotation to achieve inclined illumination of the gratings, G0, G1 and G2, leads to a scale up of all the design parameters for design energy E0. The scale up is by the factor of $1/\cos(\theta)$, with θ being the rotation angle. This results in a corresponding scale up of the primary design energy E0 by the same factor of $1/\cos(\theta)$. For instance for a gratings rotation of θ=60°, envisaged herein in an advantageous embodiment, the design energy E0 (at θ=0°) is doubled into 2*E0.

The interferometric and source grating setup is governed by certain "design rules" that must be respected. One such design rule is the requirement that:—

$$d_0/l_0 = p_2/p_0 \quad (1)$$

This is assumed to hold for the E0 at θ=0°. Fortunately, because $d_0$, $l_0$ scale together by the above mentioned common scale factor $1/\cos(\theta)$, eq (1) is preserved or is invariant under rotation. This invariance allows maintaining in particular the Talbot requirement underlying operation of the interferometer IF. In other words, denoting by $d_{eff}$, $l_{eff}$ the scaled up effective Talbot distance (that is the intra-grating path length through the interferometer) and the scaled up effective source grating distance, respectively, the following holds:—

$$d_0/l_0 = d_{eff}/l_{eff} = p_2/p_0 \quad (2)$$

However, a scaling of the source distance l0 is also unfortunate in another sense as this would mean changing the dimensioning of the X-ray apparatus in Z direction which is undesirable because of space restrictions for instance or because of a need for complex mechanism to achieve the scaling of the source grating distance l0. To obviate this requirement to scale the source distance l0, Applicant has found that design rule as per eq (2) can still be respected by a suitable adaptation of pitch of p0, say into p0'. This pitch adaptation can be used to compensate for the otherwise required scaling of the source distance l0. It is therefore proposed herein to include in the interferometric X-ray imaging apparatus, a pitch adaption mechanism SGC (not shown in FIG. 1 but see FIGS. 2, 3) combined with rotation stage RS2. The pitch adaption mechanism SGC is configured to adapt the pitch p0 of G0 to compensate for the changed intra-grating path length and to thereby maintain the source grating distance as per the design energy E0 for normal illumination at the reference inclination θ=0°. In other words, using an adapted source pitch p0', equality in eq (2) can be maintained for the same l0:—

$$d_{eff}/l_0 = p_2/p_{0'}. \quad (3)$$

Figure 2:
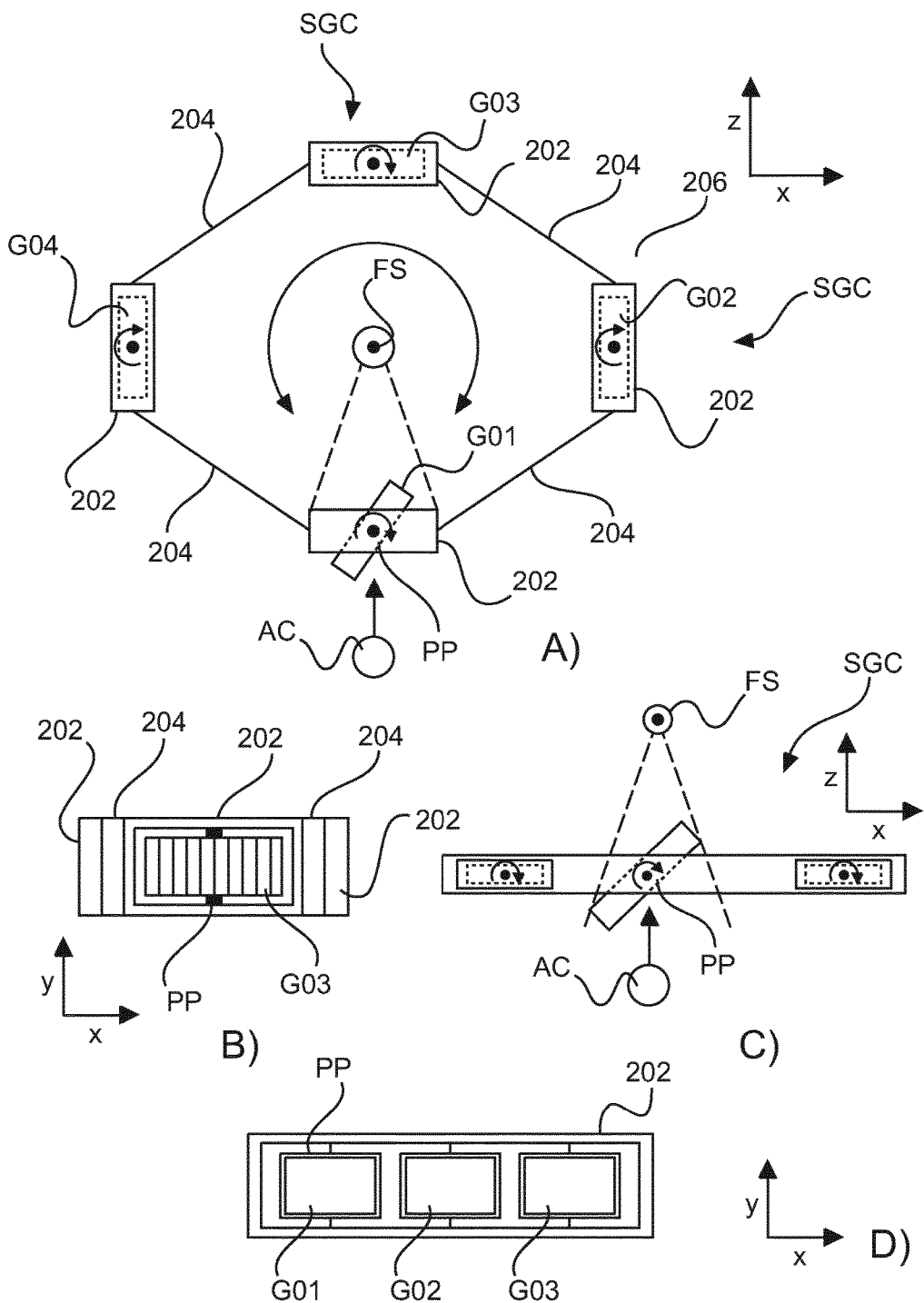
FIG. 2 shows different embodiments of a source grating adaptation mechanism.

As an illustration, suppose we use instead of $d_0$ the effective distance $d'=d_0/\cos 60° = 2*d_0$, for θ=60°. Then we have from (3) $d_{eff}/l_0 = 2*d_0/l_0 = 2*p_2/p_0 = p2/(½*p_0)$. Introducing the adapted pitch $p'_0$ for a "pseudo" grating $G'_0$ ($p'_0 = ½*p_0$), equation (3) is fulfilled as per $d_{eff}/l0 = p2/p'_0$. Thus, an increase of Talbot distance by a factor of 2 is compensated by a $G'_0$-grating having half of its primary pitch while the source grating distance l0 is maintained. In other words, by a gratings rotation of θ=60°, envisaged herein in an advantageous embodiment, the design energy E0 for θ=0° is doubled whilst the source grating distance l0 as per the θ=0° setup is maintained. In return for keeping the source grating distance constant when the gratings are rotated, the pitch of the source grating $p_0$ is halved. Of course the same reckoning will hold true for any θ but now the scaling is as per factor 1/cos(θ). For instance, a rotation by θ=45° allows to increase primary design energy E0 by roughly 40% whereas a rotation by θ=30° affords an increase by about 15%. It is of note, that previously mentioned aspect ratios also scale accordingly, which affords an enormous simplification, as there is no longer the need to use dedicated grating with specific aspect ratios for different design energies. Because of the inclined illumination effected by the rotations it is also the path through the gratings that is scaled up by the right amount. This then results in correct effective aspect ratios Referring now to FIG. 2, there are shown embodiments of the source grating adapter mechanism SGC introduced above. In the embodiments of FIG. 2, the source grating adapter mechanism exchanges, in dependence on the desired design energy, one source grating for another one having a different pitch that corresponds to the desired design energy. In other words a set of plurality of source grating is exchanged, each having a dedicated pitch that fits a respective one of design energies in a predefined set of design energies as per eq (3) above. FIG. 2 shows two different embodiments of how such an exchanger mechanism SGC can be implemented. FIGS. 2A and 2B show two different views of one embodiment with FIGS. 2C, 2D showing two different views of another embodiment. View A, C are side elevations along Y whereas views B, D are plan views along Z.

Broadly, the embodiment as per views 2A, 2B is a "revolver" structure for exchanging the source gratings whereas FIGS. 2C and 2D show a linear exchanger structure. The different gratings have each a dedicated pitch adapted for different design energies and are designated in view A as G01-G04. That is, the exchanger SGC is capable of exchanging for four different gratings but this is for illustration only and any other plurality (other than four), e.g. two, or three, or five etc. is also envisaged herein. The individual rotatability of each of the gratings may be implemented as previously explained for rotation stage RS2, the exchanger essentially implementing a plurality such rotation stages, one for each grating in the set of gratings. In other words, each source grating G01-G04 is framed in their respective framelet (not shown), each rotatably arranged in their mounting cradle 202 similar to what has been explained above at FIG. 1. The cradles 202 are interconnected by connective elements 204 to form an essentially ring or cylindrical structure which as a whole is rotatably arranged to orbit around a center point, for instance around the focal spot FS. Preferably, the revolver structure SCG is rotatable clockwise and counterclockwise to increase responsiveness of the exchanging operation. The rotation of the revolver structure SGC allows placing a desired one of the source gratings G01-G04 under the focal spot FS for exposure by the X-ray beam. Once the desired source grating has been rotated under the focal spot (when viewed along the negative z direction) and onto the optical axis, it is then the respective grating itself that is rotated by θ to adjust for the new design energy scaled up by 1/cos(0). The system is then ready for exposure. In the view of Figure A, it is currently source grating G01 that resides under the focal spot FS and rotated around θ, ready for exposure. An actuator AC effects rotation by θ of the respective framelet (with the grating therein) and around a rotation axis though the center of the respective grating as described above for rotation stage RS2. There is either a single actuator AC or each grating G01-G04 has its own actuator to effect the rotation of the gratings G01-G02 once they have been placed under the focal spot.

FIGS. 2C, 2D show a different embodiment of an exchanger mechanism where the exchange operation is effected not by revolution as in FIGS. 2A, 2B but by linear translation. Framelets with the grating structures G01-G03 therein are rotatably arranged in linear sequence in a mounting cradle 202. One or more actuators AC effect the respective rotation of the gratings as described above for rotation stage RS2. The whole structure SGC can be advanced forwards or backwards past the focal spot FS so as to place a desired one of the gratings under the focal spot FS.

Either one of the two exchanger structures as shown in FIG. 2 can be arranged for instance inside the housing of the X-ray unit or outside the housing. It should be understood that implementations as per FIG. 2 are exemplary embodiments and other suitable mechanical implementations or variants of the above are also envisaged herein.

In one embodiment, the exchanger structure SGC includes exactly two source gratings G01, G02 one being adapted in pitch to one design energy E0, the other to double the design energy 2*E0. Rotation of the source grating adapted to 2*E0 is then by θ=60°. Rotation is reset to θ=0° when exchanger SGC exchanges back for the grating whose pitch is adapted to the ("primary") design energy E0. However, other such "dual" combinations are also envisaged. For instance, a rotation by θ=45° allows to increase primary design energy E0 by roughly 40% whereas a rotation by θ=30° affords an increase by about 15%.

Figure 3:
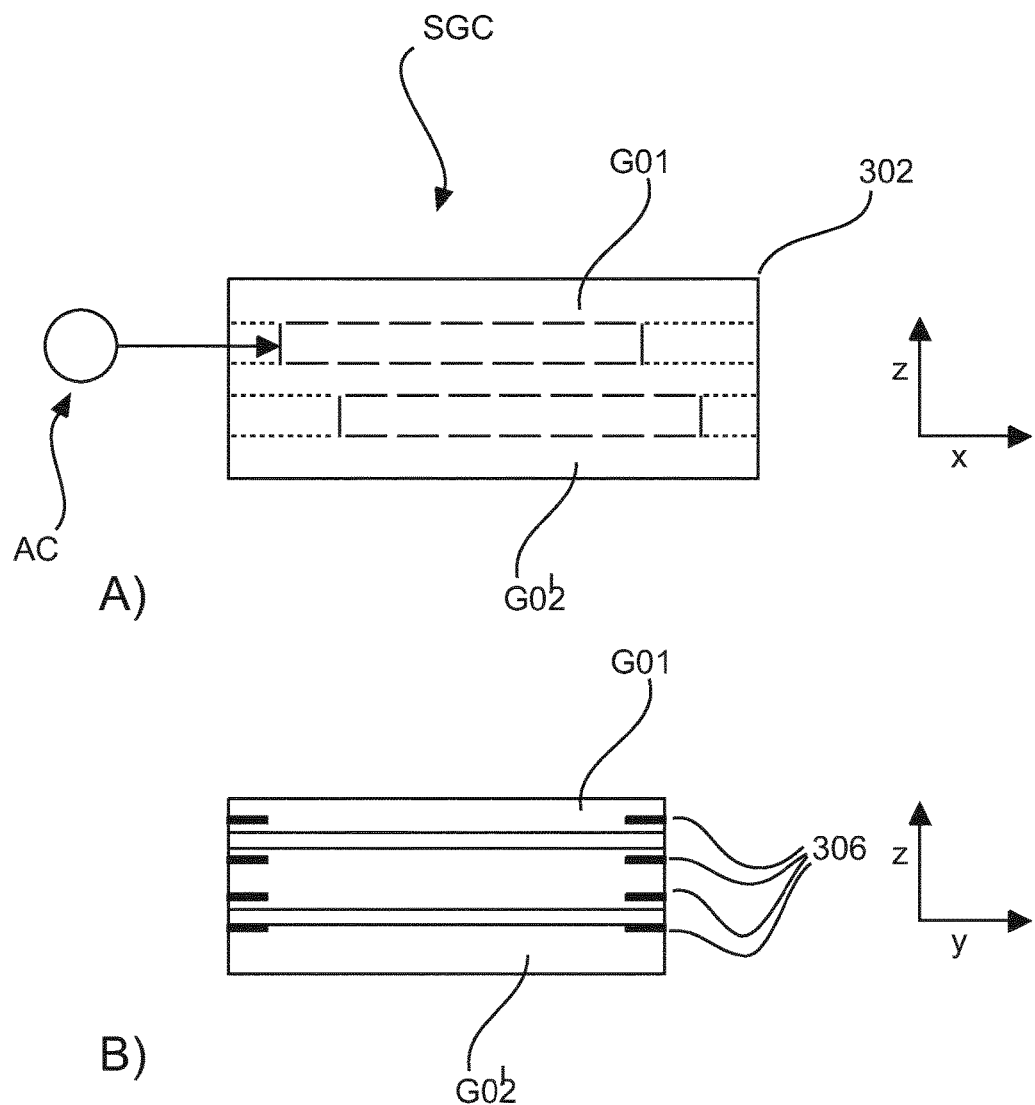
FIG. 3 shows a further embodiment of a source grating exchanger mechanism.

Turning now to FIG. 3, this shows another embodiment of the source grating adapter mechanism SGC. In this embodiment, there is no exchange operation but a first source grating is combined with a second source grating to achieve the pitch adaptation. More particularly, and in one embodiment, two gratings G01 and G02, having respective pitches p0' and p0'/2, are arranged one on top of the other in at least a partial superposition. The superposition of the gratings is such that the rulings of the two gratings are parallel, in other words the bars and trenches of the two gratings run parallel. When viewed along the optical axis, a double-decker grating structure is then formed where the two gratings are combined to overlap. When the respective bars of the two gratings are aligned in registry with each other, the pitch of the double decker grating structure at the overlap is p0'. But if a lateral displacement across the ruling directions $\Delta x=\frac{1}{2}*p0'$ of one of the gratings is effected in a direction perpendicular to the rulings so that the respective gratings are brought into anti-registry (that is, the bars of one grating block the trenches of the other grating when viewed along the optical axis), the pitch of the double decker grating structure at the overlap is now p0'/2. Therefore, the pitch of the double decker grating structure can be selectively doubled or halved by laterally moving one of the two gratings by $\Delta x$ or $-\Delta x$ to convert from first order energy E0 to second order energy 2*E0. In other words, in this embodiment a new grating structure (the overlapping region or double decker) is combined from the two gratings, and this new grating structure has an effective pitch of p0'/2 p0' depending on whether the two sets of bars are in registry or anti-registry.

With continued reference to FIG. 3, a non-limiting embodiment of lateral displacement for pitch adaptation is shown. A cage or frame structure 302 formed from material of sufficient rigidity (aluminum or hardened steel, etc.) is shown in FIG. 3, with A, B affording different views along different directions. View A shows a side elevation on the source grating adaptation mechanism SGC along Y direction (that is, along the orientation of the grating rulings), with view B being a side elevation at 900 along X direction across the directions of the rulings. Two sets of tracks 306, an upper and lower (relative to the −Z direction) are formed in side walls of the frame structure 302. The two gratings G01 and G02 are slidable relative to each other in said tracks 302. In this way, the lateral displacement of the two gratings can be facilitated. It is sufficient for only one of the gratings to be slidable relative the other (stationary one) although an embodiment where both gratings are slidable is not excluded herein. The lateral displacement is effected by an actuator AC. It is understood that the source grating adapter structure SGC is built into the rotation stage RS2 of FIG. 1. In other words, the whole of the source grating adaptation mechanism SGC is rotatable with respect to the optical axis by $\theta=60°$, in dependence at which of the (in this case two) design energies, E0 or 2*E0, one wishes to operate. As before, this rotation is effected by the actuator of stage RS2 (not shown in FIG. 3). Alternatively one single actuator may be configured to effect both, the lateral displacement and the rotation, by a suitable gearing mechanism. In accordance with eq (3), one (or both) of the source gratings G0, G02 are displaced by $\Delta x$ to achieve half the pitch p0'/2 if a scale up by 100% of the design energy is called for. If the displacement is reversed by $-\Delta x$, and the double decker grating is rotated back to $\theta=00$, the system returns to primary energy E0 configuration. The relative displacement $\Delta x$ or $-\Delta x$ of the gratings G01, G02 for the purpose of pitch adaptation can occur concurrently whilst the double decker is rotated by $+/-\theta$ or the rotation and displacement are carried out in sequence. The rotation $+/-\theta$ is about a rotation axis along the grating rulings and extends into the y direction, that is, into the plane of the drawing as per side elevation view FIG. 3A).

The rotation axis passes through the center or the interspace between the superimposed gratings G01 and G02.

Figure 4:
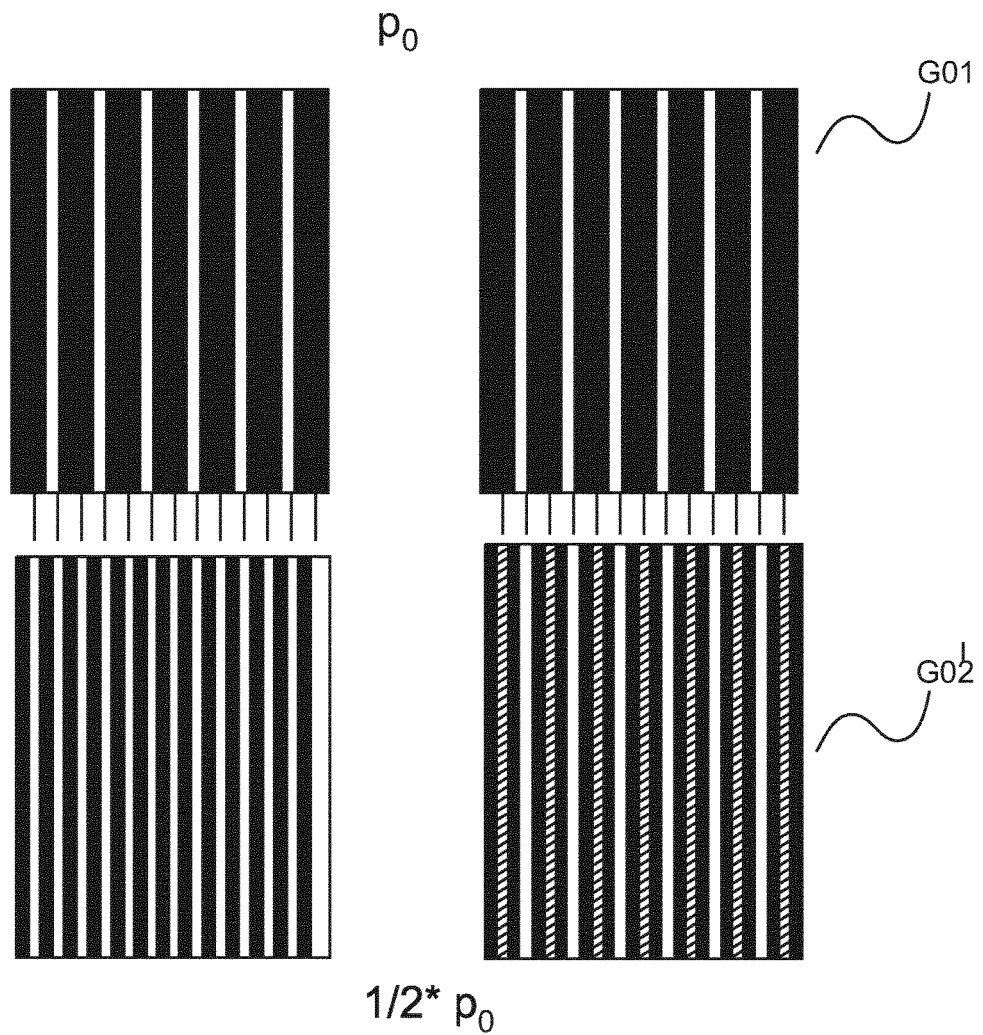
FIG. 4 shows absorber gratings having different pitches.
Figure 5:
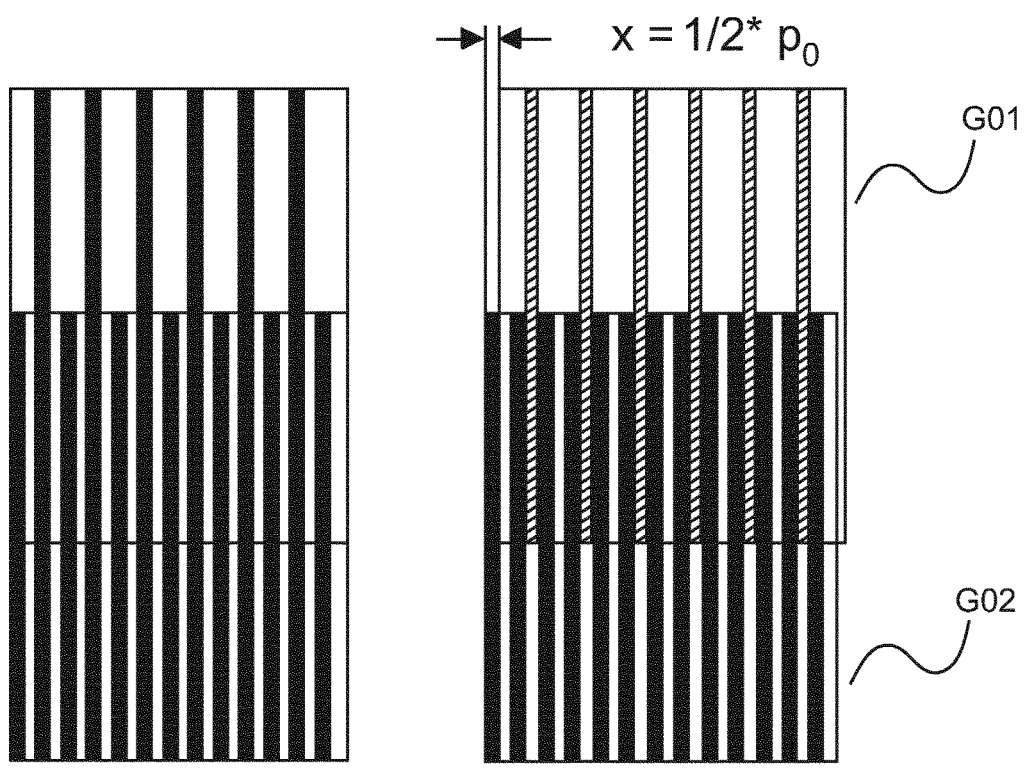
FIG. 5 shows superimposition of gratings having different pitches.

FIGS. 4 and 5 are schematic illustrations of the principle underlying operation of the source grating adapter as per FIG. 3. In FIG. 4 a $p_0$-pitch grating in the upper part and a $p'_0$-grating ($p'_0=\frac{1}{2}*p_0$) in the lower part are compared. In the lower right, every other trench of the $G'_0$ grating is blocked out and the resulting grating is a "second order" $G'_0$-grating, that is, a grating whose pitch is now adapted to double the design energy. Comparing this second order $G'_0$-grating to the upper right one, which is a (first order) $G_0$-grating, it is recognized that at least with respect to the pitches both gratings are identical. As consequence, equality in design rule equation (3) can be maintained (d'/lo=p2/$p'_0$) with the same $l_0$ and essentially the same $G_0$-grating (safe for the blocked out trenches). This mutual blocking out is sound, because all trenches of a $G_0$-grating act as a separate coherent X-ray sources, which produce their own intensity distributions (Talbot-carpets) in the space between the gratings $G_1$ and $G_2$ having all their minima and maxima at the same positions. Blocking out of some of these independent X-ray sources will then only reduce the total X-ray flux at the $G_2$-grating. A regular blocking pattern of trenches, as in the lower right of FIG. 4, will then cause a homogenous reduction of X-ray flux by half compared to when there is no blocking.

FIG. 5 is a practical implementation (as per FIG. 3) of the concept in FIG. 4. That is, the block-out of the trenches mentioned in relation to FIG. 4 is achieved by aligning the bars between the gratings in anti-registry. That is, the first order high energy grating with pitch p'0 is converted to a second order grating by the superposition of two gratings, combined with the small linear displacement relative to one another. This principle is similar to the one described in Applicant's WO2012/063169A1. As shown in FIG. 5, the two gratings are superimposed: one (G01) having a pitch p0', the other one (G02) having double the pitch 2*p0' but provided with absorbing bars, which have the same widths as the bars of the first grating G01. The gratings are so aligned that their rulings are parallel. In FIG. 5, the Y-axis runs from top to bottom and view on the gratings is in Z direction. According to FIG. 5, left hand side, if the gratings are superimposed whilst their respective bars are in registry, the overlapping area formed by the superimposed gratings will reproduce the p0'-pitch grating. But performing a slight displacement relative to one another of the superimposed grating results in a grating of double the pitch 2*p'0=p0, having the same trench width as the p0' grating and the bars now being aligned in anti-registry in the overlapping area. Thus a new source grating G0 is formed as a result of this gratings combination operation. In other words, by arranging the two gratings in at least partial superposition and by ensuring that the so formed overlapping area is within the optical axis, the pitch in the overlapping area can be changed by a relative translation of the two gratings in a direction X across the rulings.

It will be appreciated that the solution as per FIG. 3 will demand a smaller footprint as the solutions proposed in FIG. 2, in particular FIGS. 2C, 2D, because in FIG. 3 the two gratings remain essentially superimposed at all times and under the focal spot FS with only a rather minute lateral displacement $\Delta x$ required for design energy conversion between the two energy orders E0 and 2*E0. In contrast, in the exchanger mechanism as per FIGS. 2C, 2D, there is only one of the gratings under the focal spot FS at any one time, thus the footprint requirement is at least double that of the footprint in FIG. 3.

As an alternative to the embodiment in FIG. 3, a solution without lateral displacement across the ruling directions is also envisaged although this comes at the expense of a larger footprint requirement. In this embodiment, there is only a motion along the direction of the grating rulings to effect the superposition and to build up the overlapping area. The two gratings are moved so as to build up the double decker structure. In this embodiment, the gratings are already held in alignment with the two sets of bars in anti-registry as in the right side of FIG. 5. If the gratings are not yet superimposed, (left, lower side of FIG. 5) it is only the grating with the higher pitch (G02) that intersects the optical axis. If the changeover to the other (double design energy) is called for, the other grating (which is not yet intersecting the optical axis) is moved along the rulings direction to form the overlapping area of the double decker grating structure, having the lower pitch, and so as to intersect with the optical axis. The situation where the two gratings are partially overlapping is shown on the right in FIG. 5, with the bars of grating G01 shown hatched and the bars of G2 in black to better illustrate that they are in anti-registry with each other.

Although the embodiments in FIGS. 3-5 have been explained for θ=60°, that is for a doubling or halving of the design energy, it will be understood that it can be applied also to other scaling factors $1/\cos(\theta)$.

Figure 6:
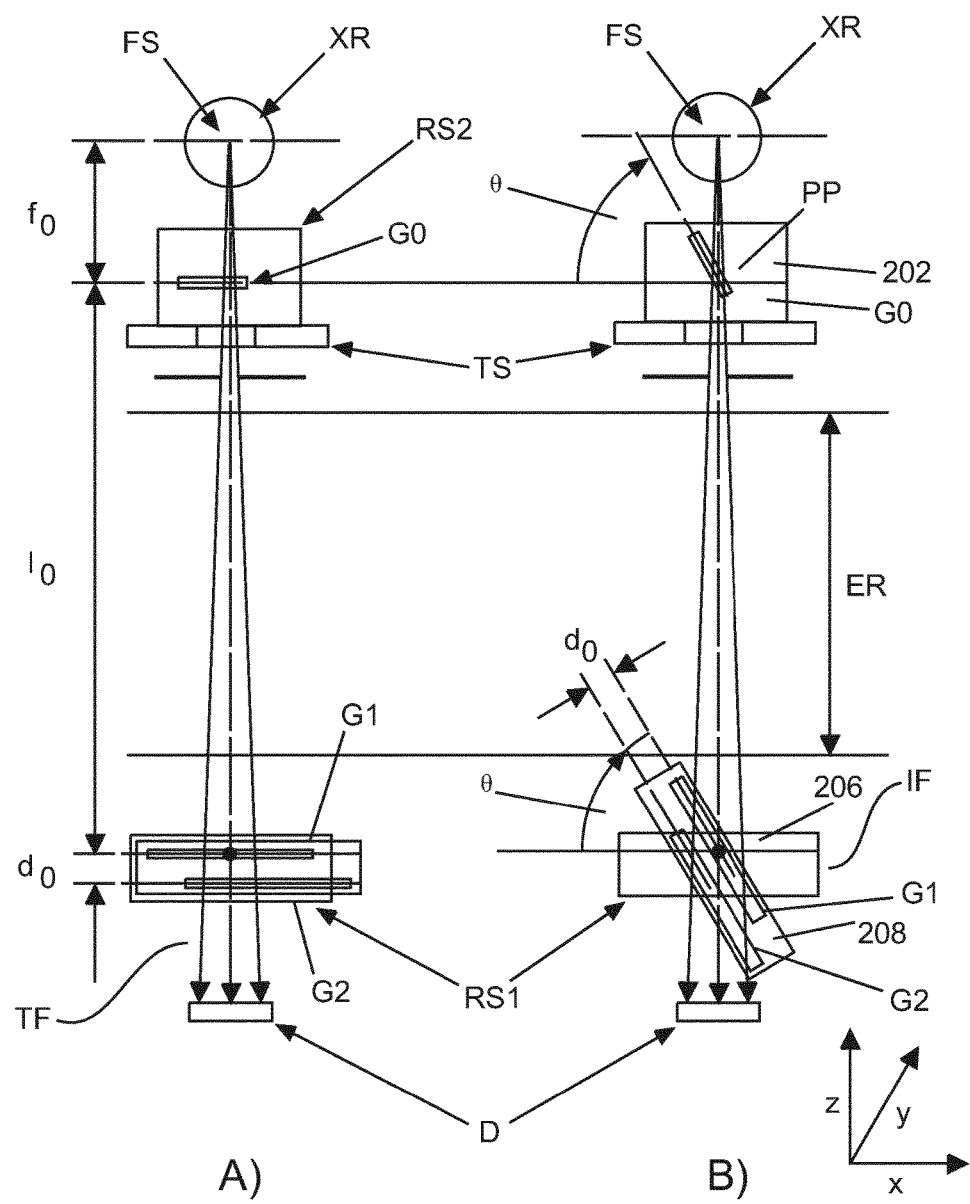
FIG. 6 shows views of different states of an X-ray imaging apparatus according to a further embodiment.

According to one embodiment and as mentioned earlier, operation of the interferometer as proposed relies on the Moiré fringe pattern having a suitably adjusted period across the effective local field of view of the interferometer. The adjustment of the Moiré period of the fringe pattern can be effected herein by using an additional translating stage in combination with the above mentioned rotation stages. The adjustment of the Moiré fringe pattern is done by mutually detuning the $G_1/G_2$ unit, combined with a translation stage that slightly adjusts $d_0$ or, preferably, $l_0$. In one embodiment, the X-ray imaging apparatus comprises an X-, Z-translation stage TS. This embodiment with the additional translation stage can be combined with any of the above described embodiments in FIGS. 1-2. Combination with FIG. 3 embodiment is also possible, however in this case care must be taken to adjust for both, pitch in the overlapping area and the fringe pattern. The translation stage affords via a suitably configured actuator, a translation along the Z-axis and along the X axis across the direction of the grating rulings. The actuator for the translation stage TS is either in addition to the RS stage actuator or a single actuator may be configured to effect both, the X, Z translations and the rotations, by a suitable gearing mechanism. In one embodiment, the translation stage TS is coupled with the rotatable interferometer $G_1/G_2$. Alternatively and preferably, the X-, Z-translation stage is combined with the rotatable $G_0$-unit as shown in FIG. 1. In a first step of fringe adjustment, the system is set to θ=0° and by using the z-stage component of the translation stage TS, the appropriate Moiré fringe direction is adjusted. In a second step, after rotation of the grating G0 or G1/G2 by θ, the X-translation component of stage TS is used for the fringe direction adjustment at the second order design energy of the system. This is due to the fact that in the case of the rotated state (e.g., θ=60°) any change Δx along the X axis of the $G_0$-grating will cause an effective change $\Delta l_{eff}$ of the $l_0$ distance according to $\Delta l_{eff}=\Delta l/\cos \theta$. It is noted here, that the X-adjustment does not affect the Δ=0° state because of the translational invariance of the grating system with respect to the x-direction across the trenches (grating trenches run parallel to the Y axis). But in order to ensure that an appropriate dynamic range of $\Delta l_{eff}$ can be achieved in order to maintain the Talbot distance versus source grating distance ratio in eq (3), it might be necessary to increase the dynamic range for the Δx displacement. When the rotation axis runs through the center of the grating as in FIG. 1, the Δx displacement range is restricted to slightly smaller than ½ the $G_0$-grating edge length along the X axis. Therefore, in FIG. 6 a variant to the embodiment in FIG. 1 is proposed, where now the rotation axis of G0 is set off-center, preferably close to one of the edges of the $G_0$-grating. Thus by asymmetric rotation, the available dynamic range $\Delta l_{eff}$ is nearly doubled compared to the symmetric embodiment of FIG. 1 where rotation of G0 is around a central axis through the G0 grating. A similar off center rotation for gratings G1 or G2 can be arranged if the translation stage TS is coupled instead to the interferometer IF.

In the following, a number of variants or additions to the above embodiments will be described.

For instance, it should be noted herein, that the above proposed design energy switching functionality by rotating the gratings, is not restricted to scanning DPCI systems but is also applicable to static DPCI systems. In the latter system, phase stepping is performed by a relative motion of the $G_1$ and $G_2$ grating perpendicular to the trench direction (here denoted as Y direction) or by a preferred motion of the $G_0$-unit relative to the $G_1/G_2$-interferometer unit. In this case of a static phase stepping system, the above described x-, z-translation stage TS further includes an X-stage translation component for translation along the X axis across the direction of the rulings. The Y-translation component can then be used for the phase stepping whereas the others are used for the fringe adjustment or pitch adaptation (FIG. 3), as described above.

Although in the above embodiment, the rotation of the gratings is effected automatically by suitable actuators, manual embodiments are not excluded herein. For instance, by suitable gearing mechanism the rotation and or translation of the gratings can be affected by operation of a suitable manual actuator for instance thumb wheel etc.

In one embodiment the X-ray imaging apparatus includes a user input device (e.g., GUI or otherwise) to select a desired design energy of the X-ray imaging apparatus. The desired energy can be expressed on term of a current design energy time the scale factor $1/\cos \theta$. The specified design energy is then received in a step S10 at a control module CC. In response to such a selection, a suitable signal is forwarded in step S20 by control module CC to the actuators of the gratings to effect a corresponding rotation θ and/or translation of the interferometer and the source gratings (if any). The control module CC may be arranged as a software module on a general purpose computing unit such as a work station. The rotation so effected corresponds to the desired design energy selected by the user. In the manual embodiment, selection of a desired design energy will indicate to the user the angle θ by which the gratings need to be tilted. The user can then use the manual actuator, such as the thumb wheel, to effect the corresponding rotation. To increase accuracy, visual guiding tools may be used to help the user when manually setting the rotation angle θ to the desired value. For instance, sensors at the gratings can pick up a current rotation angle and a visual indication thereof can be rendered on a display unit against a visual indication of the target rotation.

As a further variant to any of the above embodiments, and referring back to eqs (1-3), it may also be possible to adjust the pitch p2 of the analyzer grating instead of the pitch p0 of the source grating to ensure equality in the design equations. However, adjusting source grating pitch p0 as described above is preferable because this has been found by Applicant to be easier to implement. If a pitch adaptation mechanism for G2 is used similar to the one explained above for G0, the pitch of G1 will need to be adjusted accordingly. These alternatives are also envisaged herein. In particular, any of the above described adapter mechanisms as per FIGS. 2,3 can be applied for G2 and/or G1 instead. The linear translation solutions may be particularly suitable in this respect.

Although in the above embodiments a separate or discrete, dedicated absorber grating structure G2 was used in the interferometer IF, this may not necessarily be so in all embodiments. For instance, the analyzer grating G2 functionality can also be integrated into the X-ray detector D itself. What is more, the grating function can be entirely taken over by the X-ray detector by a careful arrangement of the pixel geometry, in particular the inter-spacing between the pixels to replicate the G2 functionality. This "hybrid" or "no-G2 grating" interferometer arrangement with a single grating G1 can be used in any one of the embodiments. In particular then, in this embodiment, it is the detector D that is tilted by θ relative to the optical axis in concert with the tiltings by the same angle of G0 and G1. In this single grating interferometer IF embodiment, the X-ray detector D preferably has a pitch sufficiently small, hence a spatial resolution sufficiently large, for detecting, i.e., adequately resolving, the interference pattern generated by the grating G1 for the purpose of differential phase contrast imaging and/or dark field imaging. For that purpose the X-ray detector may be a high resolution X-ray detector, with spatial resolution in the micrometer range or sub-micrometer range, such as 50 micrometers or more.

As a yet further variant, an interferometer IF geometry inverse to the one shown in FIGS. 1-6 may be used. In this inverse geometry interferometer, the examination region is sandwiched between the interferometer IF, that is, the Examination region ER is between grating G1 and G2 or the examination region is between G1 and the detector for the single grating interferometer embodiment. This is different to the embodiment shown in FIGS. 1, 6, where the examination region is between the source grating and the grating G1 of the interferometer IF. In the inverse geometry case, one may then arrange source grating G0 and grating G1 rotatably and together in a frame structure as described above for the rotation stage RS1.

Figure 7:
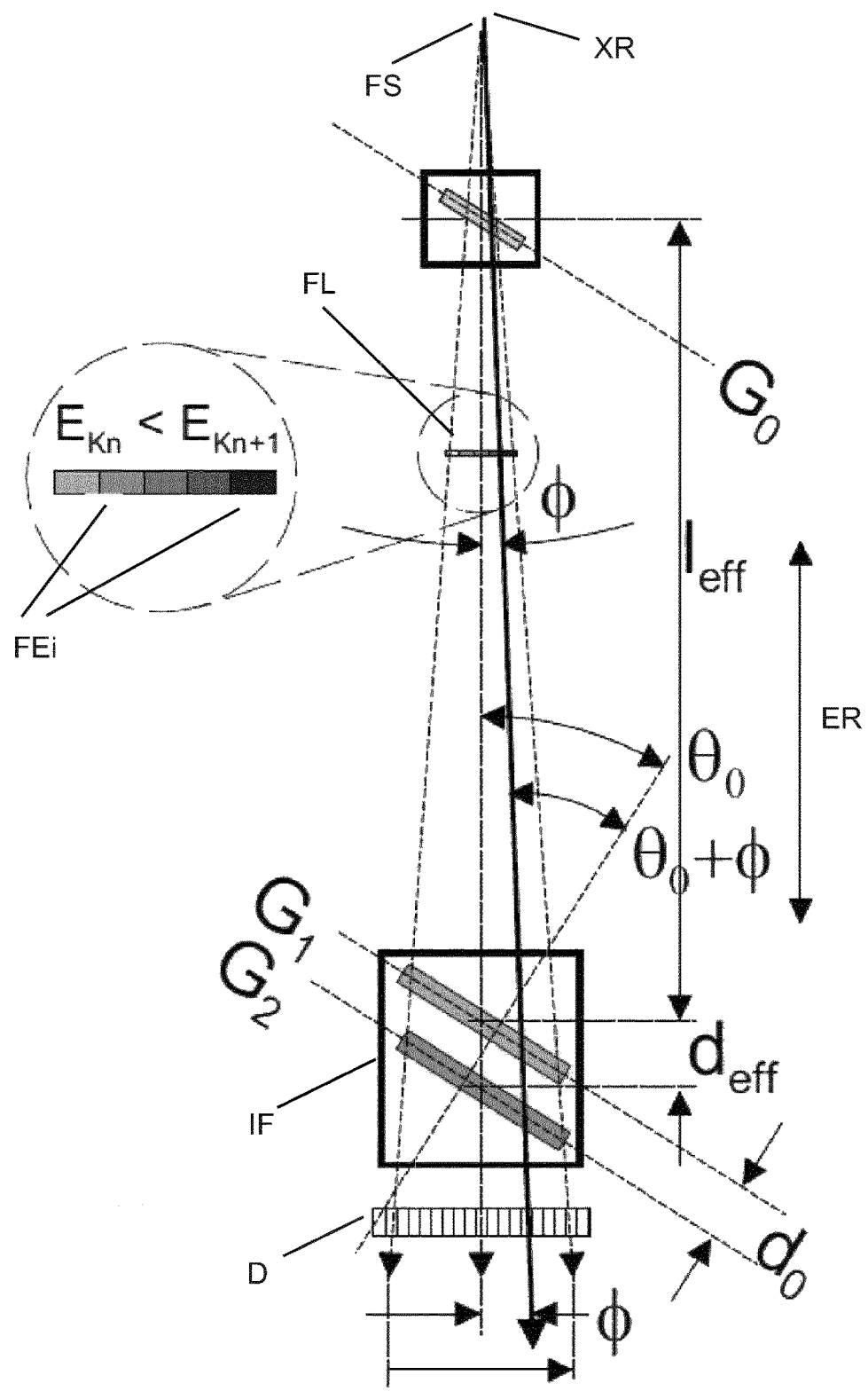
FIG. 7 shows an X-radiation filter in an X-ray imaging apparatus.

Although all of the above embodiments work well in sufficient approximation for most practical purposes, it will be noted that the design energy at the chosen inclination $\theta_0$ will hold true strictly speaking only for that part of X-ray beam that propagates along the optical axis OA as shown in FIG. 7. For rays propagating along different angles relative to the optical axis, as is the case in a fan-beam geometry rather than a parallel beam geometry, these are optimized for different design energies. More specifically, for individual X-ray beams that are not propagating along the optical axis but at a fan angle $\phi$ relative to the optical axis ($-\Delta\phi<\phi<\Delta\phi$), the effective inclination angle $\theta_{eff}$ is $\theta_{eff}=\theta_0+\phi$. For the effective design energy $E_{eff}(\phi)$ there is then a fan-angle dependence as per:

$$E_{eff}(\phi)=E_0/\cos(\theta_{eff})=E_0/\cos(\theta_0+\phi)=E_{eff}(\phi=0)*\cos(\theta_0)/\cos(\theta_0+\phi) \quad (4)$$

with $E_0$ being the ground design energy at $\phi=\theta_0$ and $\theta_0$ denoting the given tilt angle or given inclination currently assumed by the gratings. This fan angle versus design energy dependency (4) can be used to refine the proposed dual- or multi energy imaging scheme by broadening the spectral design energy window around the mean design energy for the chose inclination. For instance, in some DCPI systems, for a grating inclination of $\theta_0=60°$, a broadening of about +/−7.5% is achievable for the design energy associated with $\theta_0$.

For instance, compared to a given spectral width or "full width at half maximum" (FWHM) of a grating system of about 12 keV and a choice of the design energy at the optical axis of 33 keV, an additional variation of about 5 keV in design energy can be achieved by using the above noted fan angle versus design energy dependency. For this numerical example, an effective total energy window width of about 17 keV can be realized, ranging from about 25 to 41 keV. It has been found that the so broadened energy window excellently matches the energy dependence of the dark field signal over a large set of structural parameters.

The spectral information can be collected either by using an energy resolving detector D such as a photon counting detector, with suitable number of bins (two or more, preferably three) set up for the different design energies in the broadened range.

However, a conventional energy integrating detector may also be used instead when combined with a balanced X-radiation filter FL as shown in FIG. 7. The filter FL comprises a series of filter elements $FE_i$, each configured by material choice and/or thickness for different K-edge energies. Because of the above noted fact that the design energy varies steadily with the fan-angle, the filter elements $FE_i$ are arranged linearly across the optical axis in increasing or decreasing order of their respective K-edge energies. Whether the filter elements $FE_i$ are ordered along the x-axis in decreasing or increasing order depends on the direction of the rotation of the grating system. In the embodiment of FIG. 7, the K-edge energies $E_{Kn}$ associated with the respective filter elements $FE_i$ increase along the X-axis whilst the interferometer IF rotates clockwise.

In one embodiment, there is an uneven number of filter elements such as three or five (as in the FIG. 7 embodiment), with the element at the center arranged at the optical axis and having a K-edge energy that approximately equals to the scaled up design energy associated with the given inclination $\theta_0$. An even number of filter elements (two or more) can also be used where the K-edge energies of the two central elements straddle the design energy corresponding to the inclination $\theta_0$.

For reasons of radiation dose savings, the filter FL can be arranged anywhere in between the x-ray source XR and the object OB. In one embodiment, the filter FL is mounted above (relative to the propagating direction of the X-ray beam) or below the pre-collimator PC. Alternatively, the filter FL is mounted on top or below the G0-source grating. Alternatively, the filter FL can be arranged at the interferometer IF, either on top thereof or within the interferometer IF (ie, between the G1 and G2 gratings). Alternatively, the filter FL is mounted between the interferometer IF and the detector.

Figure 8:
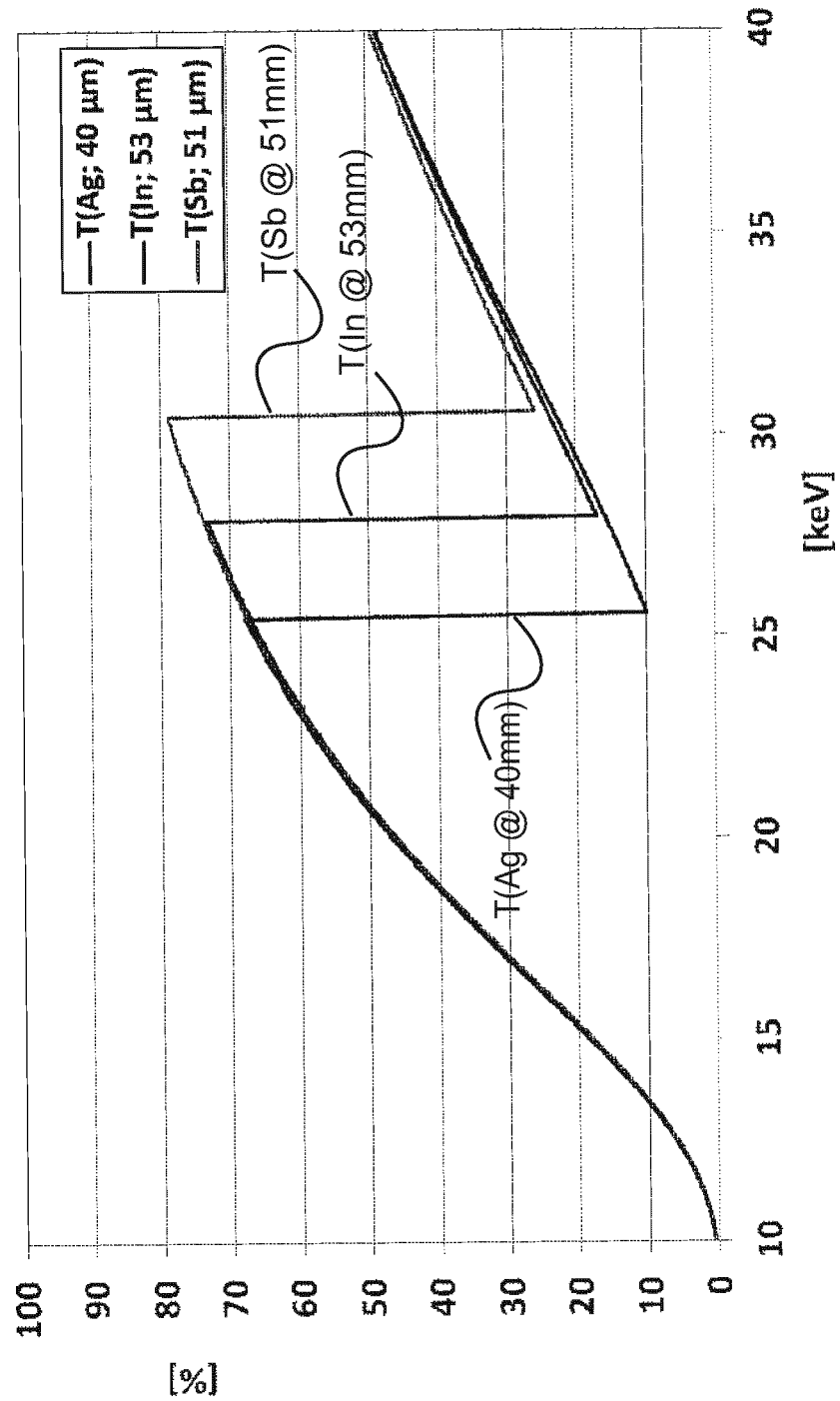
FIG. 8 shows balanced transmission curves of different filter elements.

As mentioned, to achieve better spectral separation, the materials and/or thicknesses of the filter elements $FE_i$ are configured so that the transmission functions of the respective filter elements are "balanced". In other words, the filter elements are chosen such that the respective low energy branches to the left of the K-edges are essentially coincident as shown in the diagram of FIG. 8 at the example of three transmission curves T for a filter FL whose three filter elements are formed from three different materials, namely Ag (Z=47; K-edge=25.5 keV), In (Z=49; K-edge=27.9 keV) and Sb (Z=51; K-edge=30.5 keV), having respective thicknesses. The vertical axis is the proportion (in %) of the transmitted radiation and the horizontal axis is the radiation energy in keV. Alternatively, the respective high energy branches (to the right of the K-edges) are made to essentially coincide.

Figure 9:
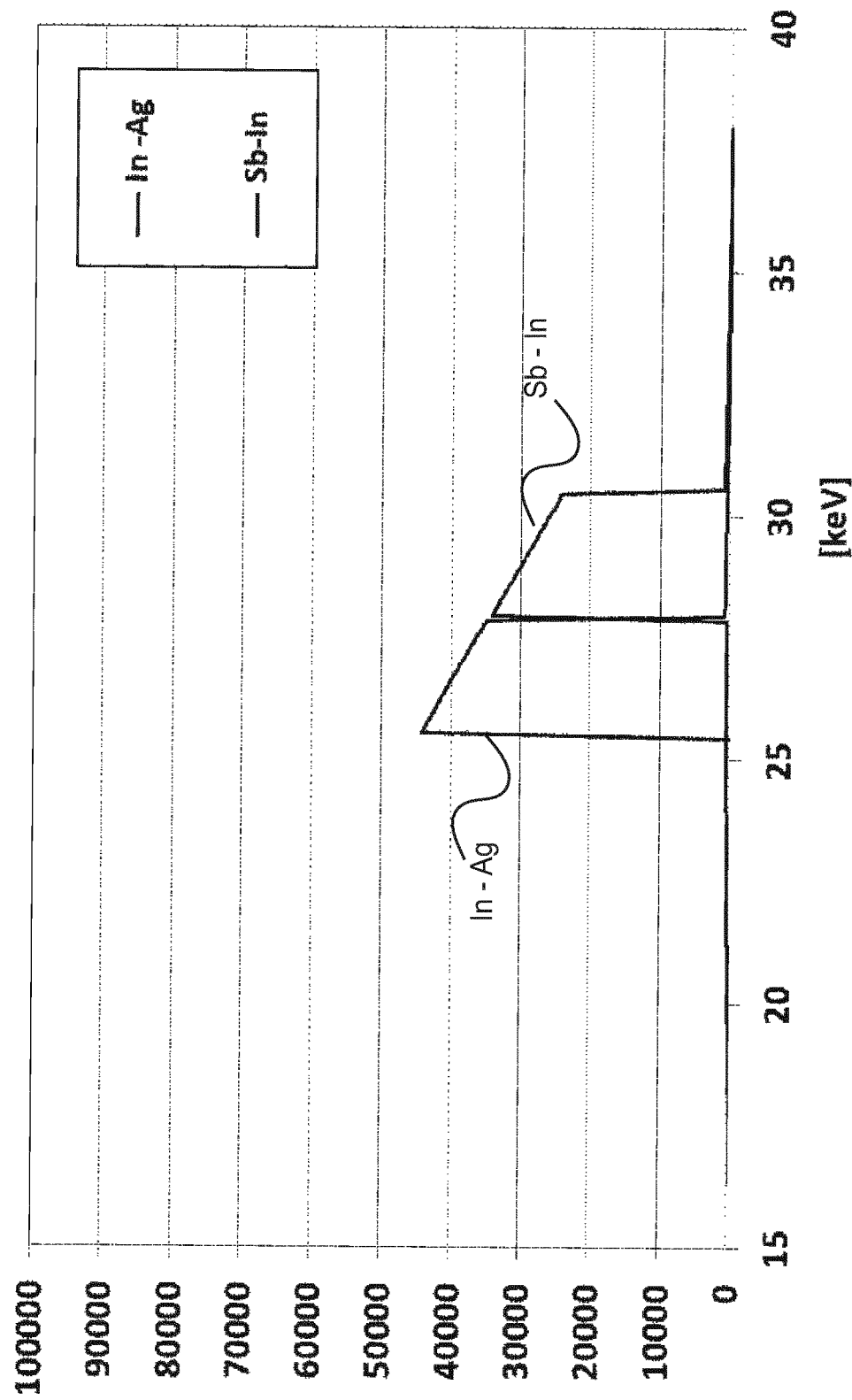
FIG. 9 shows an example of spectral information collectable when using an X-radiation filter with balanced filter elements.

By forming respective difference images from the filtered signals, a sharp spectral separation can be realized for dual or multi-energy imaging having almost no flux-contributions outside the energy windows which are defined by the K-edge energies of the K-edge filter elements. This spectral separation is exemplary shown in FIG. 9 where two respective difference signals, Sb—In and In—Ag, are shown based on the transmission functions in FIG. 8. In FIG. 9, the vertical axis represents the photon flux and the horizontal axis represents the photon energy in keV.

Suitable other material combinations and thicknesses for mammography applications include: Sn (Z=50, K-edge=29.2 keV), and Te (Z=52; K-edge=31.8 keV). Filter thicknesses of around 40 to 50 µm are suitable in this context. For other than medical applications, Cd (Z=48) may also be used. In a different photon energy region around 50 to 60 keV, suitable elements include Gd (Z=64; K-edge=50.2 keV), Tb (Z=65; K-edge=52.0 keV), Dy (Z=66; K-edge=53.8 keV), Ho (Z=76; K-edge=55.6 keV), Er (Z=68; K-edge=57.5 keV) and Yb (Z=70; K-edge=61.3 keV).

Using as an example the three-element filter formed from Ag (Gold), Sb (Antimony) and In (Indium), the equation for balancing the filter FL is given by:

$$\mu_{Ag}(E_0=25 \text{ keV})*d_{Ag(=40 \text{ }\mu m)}=\mu_{In}(E_0)*d_{In}=\mu_{Sb}(E_0)*d_{Sb} \quad (5)$$

with $E_0$ being a reference x-ray photon energy, e.g. 25 keV, and $\mu_{Ag}(E)$, $\mu_{In}(E_0)$ and $\mu_{Sb}(E_0)$ being the attenuation coefficients of the appropriate filters at energy $E_0$ and $d_{Ag}$, $d_{In}$ and $d_{Sb}$ being the balanced filter thicknesses. It should be clear that eqs (6) are applicable to any number of filter elements in any material combination. What the system (6) of balancing equations ask for is that respective ratios of the material attenuation coefficients are constant and equal to the inverse ratios of the respective thicknesses. In this example, relative to a 40 µm thickness of the Ag element, the balanced thicknesses of the In and Sb filters are 53 µm and 51 µm, respectively. In general, there is a slight mismatch in the high energy region above the K-edge thresholds. As mentioned earlier, alternatively, one could attempt matching the thicknesses of the balanced filter set the other way around by trying to make the high energy parts of the transmission curves coincide.

Due to the fact that the design energy varies with fan angle, the system IM is preferably of the scanning type because any part of the object OB one wishes to image should be exposed by the whole effective spectral width of the DPCI set up. In other words, thanks to the scanning motion in scanning type systems IM, each part of the object can be imaged by using respective rays filtered by each of the respective filter elements $FE_i$. The filter FL is moved in concert with the scanning motion. This can be implemented for instance by coupling the filter FL to the pre-collimator or to the G0-grating unit.

The broadening of the spectral window achievable by the X-ray filter FL is particularly useful for chronic obstructive pulmonary disease (COPD) detection in lung or chest dark-field imaging. By increasing the available energy window in DPCI in the described manner, more accurate information on local micro structure properties of the imaged lung tissue can be provided.

In an alternative, simpler embodiment, the X-ray filter FN comprises only a single (solid material) filter element that is arranged within the imager IM so that this single filter element $FE_1$ affects only a part of the X-ray beam. Specifically, in one embodiment, the single filter element $FE_1$ is arranged to only extend up to the optical axis OA, thus only half way across the beam at the given cross-section. The single filter element thus affects only half the X-ray beam whilst the other part passes essentially unfiltered through "air". Thus the filter comprises the single, solid part filter element part $FE_1$ and an "air part" on the other side of the optical axis OA.

Lastly, all of what has been explained in the above embodiments is of equal application for imaging system where the optical axis is movable, in particular rotatable or translatable, relative to the imaging region. Examples are CT scanners or tomosynthesis imaging apparatuses as used in mammography scanners.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above-described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium (in particular, but necessarily, a non-transitory medium), such as an optical storage medium or a solid-state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An X-ray imaging apparatus, comprising:
    an X-ray source configured to emit X-ray radiation;
    an X-ray detector configured to detect the X-ray radiation;
    an interferometer arranged between said X-ray source and said detector, said interferometer comprising at least one interferometric grating, wherein said interferometric grating is tiltable around a first axis perpendicular to an optical axis of said X-ray imaging apparatus, such that the interferometric grating is capable of being oriented at different tilt angles relative to said first axis;
    at least one source grating arranged between the interferometric grating and the X-ray source, the source grating being configured to convert the X-ray radiation into X-ray radiation with increased coherence;
    a grating adapter mechanism configured to adapt for an effective grating pitch with respect to the source grating and/or the interferometer, wherein the grating adapter mechanism is configured to i) exchange the source grating for a new source grating having a different pitch, or ii) combine said source grating with another source grating having a different pitch in order to compensate for a change in effective path length through a space between said source grating and said interferometer.

2. The X-ray imaging apparatus as per claim 1, wherein said source grating is tiltable around a second axis parallel to the first axis, so as to maintain or re-establish a spatial relationship between said source grating and the interferometric grating.

3. The X-ray imaging apparatus; as per claim 1, wherein the grating adapter mechanism combines by superimposing two source gratings or by sliding the two source gratings relative to each other when the two source gratings are at least partly superimposed onto each other, so as to form a double decker grating structure having an effective pitch that compensates for said change in the effective path length caused by either one of said tilt angles.

4. The X-ray imaging apparatus as per claim 1, wherein said tilting of the source grating and/or the interferometric grating changes a design energy of said interferometer.

5. The X-ray imaging apparatus as per claim 1, comprising a translator stage configured to translate, relative to the optical axis, the interferometric grating and/or the source grating.

6. The X-ray imaging apparatus as per claim 1, wherein the interferometer further comprises a further grating being tiltable around a third axis parallel to said first axis, so as to maintain or tare-establish a spatial relationship between said interferometric grating and/or the source grating.

7. The X-ray imaging apparatus as per claim 6, wherein the interferometric grating and said further grating are arranged on mutually opposite sides of an examination region of the X-ray imaging apparatus.

8. The X-ray imaging apparatus as per claim 6, wherein the interferometric grating and said further grating are arranged on the same side of an examination region of the X-ray imaging apparatus.

9. The X-ray imaging apparatus as per claim 1, further comprising an X-radiation filter configured to broaden a spectral window around a design energy for a given tilt angle to facilitate collection of spectral information.

10. The X-ray imaging apparatus as per claim 9, wherein the X-radiation filter comprises a plurality of filter elements configured for different energies, the filter elements being arranged across the optical axis in an ascending or descending order in sequence according to their respective energies.

11. A method for operating an X-ray imaging apparatus, comprising:
    arranging an interferometer between an X-ray source configured to emit X-radiation and a detector configured to detect the X-ray radiation, said interferometer comprising at least one interferometric grating that is tiltable around a first axis perpendicular to an optical axis of said imaging apparatus, the interferometric grating being capable of being oriented at different tilt angles relative to the first axis;
    arranging at least one source grating between the interferometric grating and the X-ray source, the source grating being configured to convert the X-ray radiation into X-ray radiation with increased coherence;
    configuring a grating adapter mechanism to adapt for an effective grating pitch with respect to the source grating and/or the interferometer;
    receiving a specification of a design energy for the X-ray imaging apparatus; and
    in response to the design energy, tilting the interferometric grating and/or the source grating around the first axis, wherein the grating adapter mechanism is configured to i) exchange the source grating for a new source grating having a different pitch, or ii) combine said source grating with another source grating having a different pitch in order to compensate for a change in effective path length through a space between said source grating and said interferometer.

12. A non-transitory computer-readable medium having one or more executable instructions stored thereon, which, when executed by a processor, cause the processor to perform a method for operating an X-ray imaging apparatus, the method comprising:
    arranging an interferometer between an X-ray source configured to emit X-radiation and a detector configured to detect the X-ray radiation, said interferometer comprising at least one interferometric grating that is tiltable around a first axis perpendicular to an optical axis of said imaging apparatus, the interferometric grating being capable of being oriented at different tilt angles relative to the first axis;

arranging at least one source grating between the interferometric grating and the X-ray source, the source grating being configured to convert the X-ray radiation into X-ray radiation with increased coherence;

configuring a grating adapter mechanism to adapt for an effective grating pitch with respect to the source grating and/or the interferometer;

receiving a specification of a design energy for the X-ray imaging apparatus; and in response to the design energy, tilting the interferometric grating and/or the source grating around the first axis, wherein the grating adapter mechanism is configured to i) exchange the source grating for a new source grating having a different pitch, or ii) combine said source grating with another source grating having a different pitch in order to compensate for a change in effective path length through a space between said source grating and said interferometer.

\* \* \* \* \*